US005641754A

United States Patent [19]
Iversen

[11] Patent Number: 5,641,754
[45] Date of Patent: Jun. 24, 1997

[54] ANTISENSE OLIGONUCLEOTIDE COMPOSITIONS FOR SELECTIVELY KILLING CANCER CELLS

[75] Inventor: Patrick L. Iversen, Omaha, Nebr.

[73] Assignee: The Board of Regents of The University of Nebraska, Lincoln, Nebr.

[21] Appl. No.: 179,655

[22] Filed: Jan. 10, 1994

[51] Int. Cl.$^6$ .............................. A61K 48/00; C12Q 1/68; C12P 19/34

[52] U.S. Cl. .............................. 514/44; 435/6; 435/91.1; 435/172.1; 536/23.1; 536/24.5

[58] Field of Search .............................. 435/91.1, 6, 91.3, 435/91.4, 172.1, 172.3, 240.2; 536/23.1, 24.5; 514/44

[56] References Cited

PUBLICATIONS

Stull et al., Pharm. Res. 12:465 (1995).
Kastan, "Participation of p53 Protein in the Cellular Response to DNA Damage", *Cancer Research*, Dec. 1, 1991, 51:6304–6311.

*Primary Examiner*—John LeGuyader
*Attorney, Agent, or Firm*—Zarley, McKee, Thomte, Voorhees & Sease

[57] ABSTRACT

The present invention relates to methods and compositions for the treatment of cancer using an oligonucleotide and an hydroxyl radical up-regulator. The oligonucleotide is characterized by its ability to down-regulate the path by which the cell repairs oxidative damage to its DNA. Thus, the oligonucleotide renders the tumor cells more susceptible to eradication upon exposure to the hydroxyl radical up-regulator administered substantially concomitantly with or subsequent to administration of the oligonucleotide. This novel treatment, preferentially inhibits the proliferation or kills malignant cells but not normal cells. Preferably, the oligonucleotide is antisense to the gene which encodes protein p53, although other antisense oligonucleotides can also be used. The invention also includes novel conjugates of the oligonucleotide and the hydroxyl up-regulator, as well as new oligonucleotides.

11 Claims, 3 Drawing Sheets

ANTISENSE OLIGONUCLEOTIDE COMPOSITIONS FOR SELECTIVELY KILLING CANCER CELLS

FIELD OF THE INVENTION

The present invention relates to methods and compositions for the treatment of cancer using an oligonucleotide and an hydroxy radical up-regulator. The oligonucleotide is characterized by its ability to down-regulate the path by which the cell repairs oxidative damage to its DNA. Thus, the oligonucleotide renders the tumor cells more susceptible to eradication upon exposure to the hydroxy radical up-regulator, preferably administered substantially concomitantly with or subsequent to administration of the oligonucleotide. This novel treatment, preferentially inhibits the proliferation or kills malignant cells but not normal cells. Preferably, the oligonucleotide is antisense to the gene which encodes protein p53, although other antisense oligonucleotides can also be used. The invention also includes novel conjugates of the oligonucleotide and the hydroxy up-regulator, as well as new oligonucleotides. In addition, the present invention provides a method of treating cancer by preferentially inducing p53 independent apoptosis in cancer cells.

BACKGROUND OF THE INVENTION

Recent investigations have revealed the great potential of oligonucleotide and oligonucleotide analogues as chemotherapeutic agents (see P. Miller and P. Ts'o, *Ann. Rep. Med. Chem.* 23: 295, 1988; G. Zon, *Pharm. Res.* 5: 539, 1988). As reported by Matsukura and colleagues (*Proc. Natl. Acad. Sci. USA* 84: 7706, 1987), certain analogues of oligonucleotides whose normal backbone structure has been changed from phosphodiester to phosphorothioate linkages are capable of potent inhibition of the replication of the human immunodeficiency virus (HIV). More recently, Matsukura et al (*Proc Natl Acad Sci USA* 68: 4244, 1989) have shown that the expression of specific HIV genes can be regulated with phosphorothioate oligonucleotides. Also, the results of a F&DA approved Phase I clinical trial of systemic administration of OL(1)p53 (SEQUENCE ID NO: 1) in refractory acute myelogenous leukemia and advanced myelodysplastic syndrome are reported by P. L. Iversen et al (J Am Soc Hem., Nov. 15, 1993 Supplement, page 443a, abstract 1757).

Until discovered by the present inventor, however, it was not recognized that the binding of oligonucleotides, of various sizes, to the outer membrane surface of biologically living cells could lead to the production of deleterious mutational events in the cell targeted by the oligonucleotide. This finding prompted a search for potential mechanisms by which the binding of an oligonucleotide to a targeted cell could lead to mutational events. Subsequent experimentation led to the discovery that large amounts of reactive free hydroxy radicals (OH$^-$) were released by the cell which bound the oligonucleotide. (See Patrick L. Iversen U.S. patent application Ser. No. 07/735,067, filed Jul. 25, 1991 entitled INHIBITION OF MUTAGENICITY INDUCED BY BINDING OF OLIGONUCLEOTIDES TO CELLS.)

Considerable evidence exists in the art that free oxygen radical species have highly mutagenic capabilities. The unexpected release of reactive oxygen radicals (especially free hydroxy radicals) by cells following the binding of oligonucleotides to the surface of those cells is in stark contrast to prior understanding of the biological consequences of binding of oligonucleotides to cell membranes.

Partially reduced forms of oxygen arise continually in all cells as products of normal metabolic pathways. Such highly reactive oxygen intermediates can be highly toxic, however, if they are not immediately inactivated or utilized in metabolic pathways. For example, in a cell, a common pathway for the complete reduction of one molecule of $O_2$ is to form water in a four-electron transfer process. However, cellular metabolic pathways also continually generate incompletely reduced species of oxygen. A one-electron reduction of $O_2$ yields superoxide ion, $O_2^-$; an additional electron yields hydrogen peroxide, $H_2O_2$; and a third electron yields a hydroxy radical, $OH_2^-$, and a hydroxide ion. These so-called "reactive oxygen radicals" are far more reactive, and hence potentially much more toxic, than is $O_2$ itself.

Hydroxy radicals, in particular, are extremely reactive and represent the most active mutagen derived from ionizing radiation. The radical is highly electrophilic and reactive, with a capacity to bind to DNA to produce modified bases, such as 8-hydroxyguanine, and thymine glycol. The former has been detected in DNA isolated from tissues exposed to ionizing radiation or to hydrogen peroxide ($H_2O_2$) (Kasai et al., *Carcinogenesis* 7: 1849, 1986). The latter, which is an oxidation product of thymine residues in DNA, is often found in the urine of individuals who have suffered DNA damage (B. Ames, *Science* 221: 1256–1264, 1983).

It is known in the art that hydroxylated derivatives of DNA are generated continuously by normal cellular metabolism, and that such modified DNA is most commonly repaired by unscheduled DNA synthesis. If, however, the modified DNA bases remain unrepaired, the consequences of the random DNA damage can include (i) mutagenesis due to erroneous replication of damaged DNA nucleotide base templates, and/or (ii) cell death due to inability of the cell to replicate its genome past a damaged DNA site. The generation of excessive amounts of reactive oxygen intermediates can, therefore, have serious ramifications for the host organism.

Most cells normally contain one or more enzyme systems which very rapidly combine with and inactivate excess reactive oxygen species. One of the major enzyme systems in this regard is the superoxide dismutase (SOD) family of metalloenzymes. Superoxide dismutase detoxifies two molecules of superoxide simultaneously, oxidizing one molecule while reducing the other:

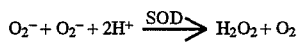

$$O_2^- + O_2^- + 2H^+ \xrightarrow{SOD} H_2O_2 + O_2$$

One form of this metalloenzyme is found in the cytoplasm of eukaryotic cells and contains copper and zinc; a different form is found both in mitochondria and in bacterial cells, and contains manganese; and another related iron-containing form is found in some bacteria, cyanobacteria, and some plants (see, for example, C. K. Matthews and K. E. van Holde, *Biochemistry*, The Benjamin/Cummings Publishing Company, Inc., Redwood City, Calif., 1990). The wide occurrence of SOD enzymes is confirmation of the biological necessity of rapid inactivation of reactive oxygen intermediates.

Hydrogen peroxide ($H_2O_2$), another highly reactive oxygen species, is inactivated by at least two different enzyme systems. The most commonly utilized is the enzyme catalase, which is a heme protein widely distributed in cells.

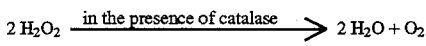

$$2 H_2O_2 \xrightarrow{\text{in the presence of catalase}} 2 H_2O + O_2$$

The reaction involves oxidation of one molecule of $H_2O_2$ and reduction of another. The extremely high turnover rate of this enzyme (more than 40,000 molecules utilized per second) confirms the importance of removing excess hydrogen peroxide from the cellular micro-environment.

Another family of hydrogen peroxide scavengers is the peroxidases which reduce $H_2O_2$ to water while simultaneously oxidizing an organic substrate. For example, erythrocytes contain a selenium-containing enzyme, glutathione peroxidase (GSH), which reduces $H_2O_2$ to water while simultaneously oxidizing the glutathione:

Glutathione peroxidase contains one residue per mole of an unusual amino acid, selenocysteine, an analog of cysteine that contains selenium in place of sulfur. Glutathione synthetase and glutathione reductase are further examples of this family of scavengers.

Lastly, it is known in the art that $H_2O_2$ is chemically inactivated by mannitol, with which it forms a stable, equimolar compound. For the purposes of this invention hydroxy, $H_2O_2$, and superoxide ion are considered to be interchangeable.

Other chemical constituents which are well known in the art for their anti-oxidant potential are such chemicals as, for example, vitamin A (Retinol and retinoic acid); vitamin E (alpha-tocopherol); Vitamin C (ascorbic acid); and the trace mineral element selenium, all of which serve in a variety of tissues and bodily processes as general reducing agents.

Cancer cells, particularly those which are malignant, exhibit elevated levels of free hydroxy radicals. These and other types of diseased cells do not exhibit the same degree of anti-oxidant protection as do normal cells. In particular, such cells are notably deficient in the scavenger protection systems discussed above. Because of this fact, irradiation kills cancer cells preferentially to normal tissue and conventional radiation therapy attempts to exploit this mechanism of action, as do certain conventional chemotherapeutic agents, such as the nitrosoureas, e.g., BCNU (bis-chloroethylnitrosourea), and the anthracycline cytotoxic antibiotics, doxorubicin and daunorubicin.

However, the sensitivity of a cell and the resultant cellular response to ionizing radiation depends primarily on the presence or absence of oxygen within the cell and upon the stage of division which the cell is in at the time of irradiation. In radiation therapy, production of oxidative damage is initiated by a dose of radiation. Cells which are oxygen-rich and sensitive to radiation will be killed more effectively and efficiently than cells which are oxygen-deficient. It appears that the molecular pathways responsible for inherent radiation sensitivity involve the initiation and production of oxidative damage, cellular sensing of the damage, and cellular response to and repair of the damage. Repair of radiation damage is most likely an enzymatic process and radiobiologists have examined the role of certain enzymes which are responsible for the detoxification of cytotoxic oxygen-related free radicals. (Golfman T. E., et. al., Cancer Research, 50: 7735-7744, 1990)

Within the cell cycle is an arrest stage, which allows the cell to stop its growth mechanism for a period of time long enough to repair any DNA damage which is detected. In the repair process, segments of DNA which contain an altered base can be recognized and repaired. When an irradiated mutant (i.e. cancerous) cell is given time to repair, the mutated DNA will be allowed to continue in its division and replication, thus proliferating the cancer or tumor.

The cellular repair mechanism is located between the $G_1$ and S phase of the cell cycle. The gene p53 has been postulated to play a role in the repair of damaged DNA and is in fact considered to function as a cell cycle checkpoint after irradiation. (Lee, J. M., and Bernstein A, Proc. Nat. Acad. Sci., 90(12): 5742-5746, 1993). Apoptosis is part of normal development and also can be triggered by DNA damage, such as that delivered by radiation and some chemicals, including those used in chemotherapy. It has been shown that levels of p53 protein rise dramatically after DNA damage. Consequently, p53 is currently believed to be crucial to the apoptotic pathway induced by DNA damage.

SUMMARY OF THE INVENTION

In accordance with this invention, and contrary to the above belief, the present inventor has found that oligonucleotides which are antisense to p53 (and hence inhibit its activity) produce apoptosis ex vivo and in vivo in treated cells via an additional apoptosis pathway, which is p53 independent.

Furthermore, in accordance with this invention, it has been found that in order to effectively treat cancer with an oligonucleotide, the cancer cell must be exposed to an oligonucleotide which acts as an oxidative repair path downregulator. Exemplary of such oligonucleotides are those which are antisense to p53. These and other oligonucleotides, for example, oligonucleotides antisense to: p21 (see PCT International Publication WO 93/12251), CDC-2, CDK (cyclin-dependent kinases), or DNA polymerase B are discussed more fully hereinafter.

In addition to exposure to the oligonucleotide of this invention, the cancer cell must also be exposed to conditions which increase the net reactive oxygen content in a cell. Such conditions are produced, for example, by exposure of the cancer cell to radiation, or an agent capable of radical oxygen induced cytotoxicity, such as for example, anthracycline cytotoxic antibiotics (e.g., doxorubicin), BCNU, BSO (buthionine sulfoxamine), hydrogen peroxide, or antisense oligonucleotide inhibitors of SOD (superoxide dismutase), catalase, GSH synthetase, GSH reductase, or GSH peroxidase.

Thus, in a preferred embodiment the present invention provides a method for selectively killing cells characterized by p53 expression in cells in vivo or ex vivo. The method comprises administering to a mammalian or human host, or to cells harvested from such host, an oligonucleotide with a sequence complementary to p53 mRNA and an agent capable of increasing radical oxygen induced cytotoxicity. The oligonucleotide and agent can be administered substantially concomitantly or sequentially with either therapeutic agent being given first. However, best results are achieved when the oligonucleotide is administered sufficiently in advance to permit therapeutic blood levels to be achieved. The antisense p53 eliminates the p53 mediated G1 checkpoint of the cell cycle, which results in an increase in the sensitivity if the targeted cells have oxidative DNA damage. Consequently, upon exposure of the cells by an agent which acts to increase radical oxygen in the cell, the cell death mediated by the anti-p53 oligonucleotide is increased dramatically, leading to delayed p53 independent apoptosis of the targeted cells with little or no adverse effect on normal tissue (as normal tissue has greater oxygen scavenging activity).

The anti-p53 oligonucleotide has a nucleotide sequence complementary to at least a portion of the mRNA transcript of the human p53 gene and is hybridizable to the mRNA transcript. In a preferred embodiment, the oligonucleotide comprises between about a 10-mer and about a 30-mer oligodeoxyribonucleotide containing a sequence selected from the group consisting of:

5'-CCCCTGCTCCC CCCTGGCTCC-3'
SEQUENCE ID NO: 1

5'-AGCAGGGCTC ACTCCAGC-3'
SEQUENCE ID NO: 2

The agent capable of radical oxygen induced cytotoxicity can be, for example, a radiosensitizer, a chemotherapeutic agent which generates radical oxygen, or any oligonucleotide capable of interaction with cells of the host causing the formation of hydroxy radicals (e.g., see Patrick L. Iversen U.S. patent application Ser. No. 07/735,067, filed Jul. 25, 1991 entitled INHIBITION OF MUTAGENICITY INDUCED BY BINDING OF OLIGONUCLEOTIDES TO CELLS the contents of which is incorporated herein by reference). A number of cytotoxic agents that have a lethal effect on target cells within the patient, wherein the lethal effect may be enhanced by one or more sensitizing agents, may be used in the method of the invention. Included are radiation (whether the radiation therapy is delivered internally or administered by external means) and cytotoxic drugs. Examples of some of the many such drugs are nitrogen mustards such as L-phenylalanine nitrogen mustard (melphalan), anthracycline chemotherapeutics such as daunorubicin and doxorubicin, platinum compounds such as cis-diamino dichloro platinum (cisplatin).

Internally delivered radiation includes therapeutically effective radioisotopes injected into a patient. Such radioisotopes include, but are not limited to, the radionuclide metals $^{186}$Re, $^{188}$Re, $^{64}$Cu, $^{67}$Cu, $^{109}$Pd, $^{212}$Bi, $^{203}$Pb, $^{212}$Pb, $^{211}$At, $^{97}$Ru, $^{105}$Rh, $^{198}$Au, $^{199}$Ag, and $^{131}$I. These radioisotopes generally will be bound to carrier molecules (e.g., are in the form of a chelate-antibody conjugate) when administered to a patient. Examples of suitable internally delivered radiotherapeutic agents are the metal radionuclide chelates which are conjugated to antibodies as described in European Patent Application Publication No. 188,256. Radiation administered by external means includes external beam radiation such as cobalt therapy.

The choice of sensitizing agent depends on such factors as the particular type of tumor to be treated and the desired cytotoxic agent to be administered. For example, certain drugs have been reported to sensitize cells to therapeutic radiation, as discussed above. U.S. Pat. No. 4,628,047 reports the use of diltiazem (chemical name: d-3-acetoxy-cis-2,3-dihydro-5-[2-(dimethylamino)ethyl]-2-(p-methoxyphenyl)-1,5-benzo-thiazepin-4(5H)-one) to enhance the sensitivity of a variety of types of cancer cells toward cytotoxic agents such as doxorubicin. *Important Advances in Oncology* 1986, DeVita et al editors, J.B. Lippincott Co., Philadelphia, pages 145–157 (1986) includes discussions of other pairings of sensitizers with certain cytotoxic drugs as well as expected differences in the susceptibility of different types of cancer cells to treatment with these agents.

A preferred sensitizer is BSO, a synthetic amino acid that inhibits gamma-glutamylcysteine synthetase and leads to a marked decrease of glutathione (GSH) in cells. Thus, BSO is thought to function as a sensitizer for drugs that have a cytotoxic effect that is enhanced by decreasing cellular glutathione levels. Especially preferred is the L-S-isomer of BSO, which has utility in depleting glutathione in the cell (see U.S. Pat. Nos. 5,171,885 and 5,245,077). BSO is available from Chemical Dynamics Corporation, South Plainfield, N.J.

Additional combinations of sensitizers and cytotoxic agents may be identified through such methods as in vitro assays using cultured cells which correspond to the desired target cells (e.g., a specific cancer cell line). Assays for determining whether BSO is effective in lowering glutathione synthetase levels in a particular type of cell line have been developed (Cancer Treatment Reports, Vol. 69, No. 11, pp 1293–1296 [1985]).

Another embodiment of this invention provides novel conjugates comprising the oligonucleotide bound through a suitable linking moiety to a suitable sensitizing agent, such as buthionine sulfoxamine or superoxide dismutase and the like, such that upon exposure to the target cells it is able to increase the concentration of hydroxy radicals to which the cellular DNA of the host is exposed. A synthetic scheme for conjugating BSO to an antibody is disclosed in U.S. Pat. No. 5,112,954. This chemistry can be used for conjugating BSO, and any sensitizer containing similar functional groups, to the oligonucleotides of this invention. The disclosure of U.S. Pat. No. 5,112,954 is hereby incorporated herein in its entirety by reference. Thus an embodiment of this invention is a conjugate represented by the following formula:

R-L-X wherein R represents an antisense oligonucleotide having a sequence essentially complementary to a sequence of RNA transcribed from a target gene selected from the group consisting of p53, p21, glutathione synthetase, and a DNA polymerase involved in repair of oxidative DNA damage; L represents a linking moiety, preferably selected from those disclosed in U.S. Pat. No. 5,112,954 (see also Iversen et al, J Gen Virol. 1989 October; 70(Pt 10): 2673–82), and X represents an agent capable of radical oxygen induced cytotoxicity.

Upon administration of the conjugate, the oligonucleotide will bind to the cellular membrane and release the biologically active sensitizing agent. The result is an increase in the number of hydroxy radicals within the cell and a decrease in the ability of the cell to scavenge oxygen radicals within the cell.

The oligonucleotide increases the cell's sensitivity to the increased amount of hydroxy radicals by inhibiting the function of the p53 gene. Inhibition of the p53 gene results in a failure of the cell to arrest its cycle at the G1 checkpoint and prevents DNA repair. The cell will continue its cycle, inducing cell death via apoptosis, due to the excessive amount of unrepaired DNA damage. The target cells may be cancer cells such as leukemia cells or any cancer which produces elevated levels of p53 are susceptible to this therapeutic regimen.

BRIEF DESCRIPTION OF THE FIGURES

The Figures show the results of a flow cytometry study to examine the effects of an oligonucleotide on cell death. The addition of OL(1)p53 to primary AML cell culture increases the rate of cell death via apoptosis in the culture. $A_o$=percent of apoptotic cells; $D_u$=percent of intact, proliferating cells.

DETAILED DESCRIPTION OF THE INVENTION

Figure 1:
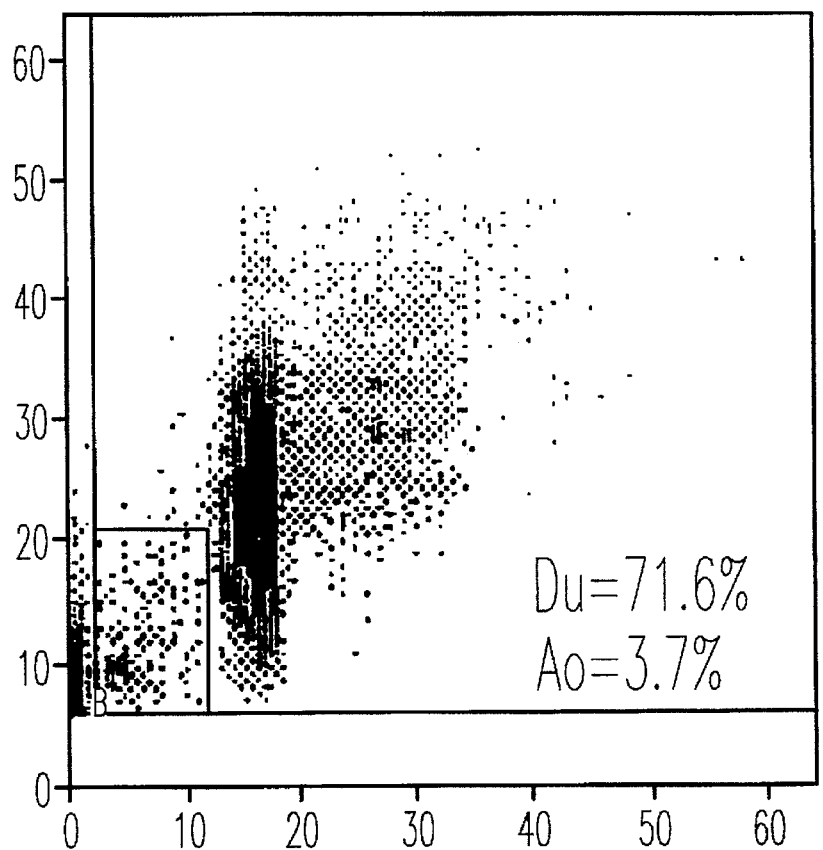
FIGS. 1, 3, 5 represent patient cells prior to incubation with OL(1)p53 (SEQ ID NO: 1) ex-vivo.
Figure 2:
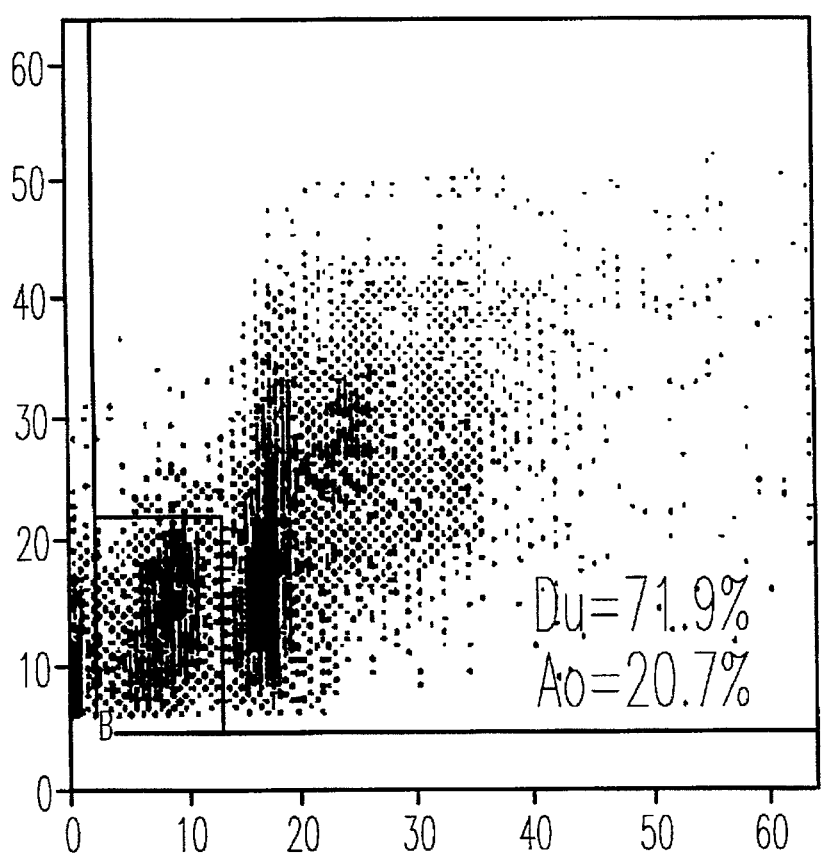
FIGS. 2, 4, 6 represent patient cells following 10 day incubation with iμM OL(1) p53. The insert box in the lower left indicates the $A_o$ region.
Figure 3:
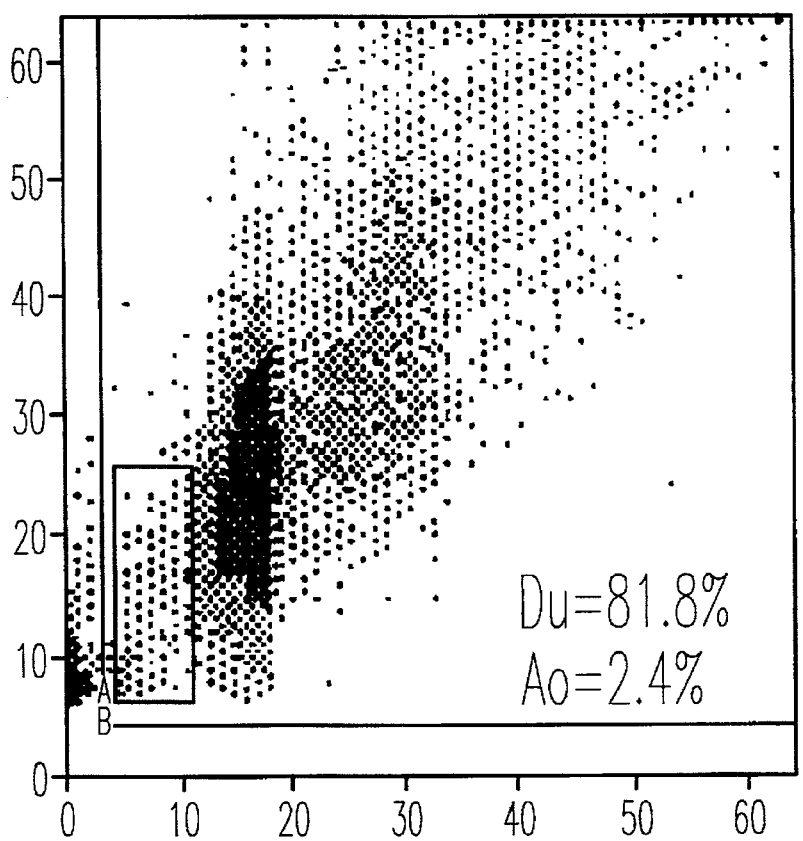
Figure 4:
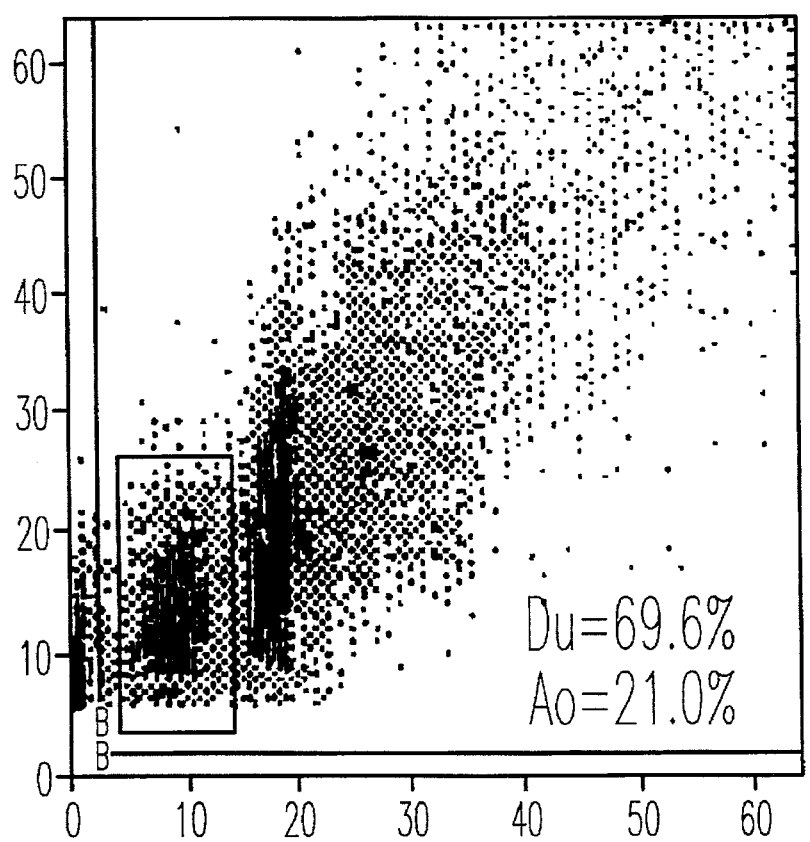
Figure 5:
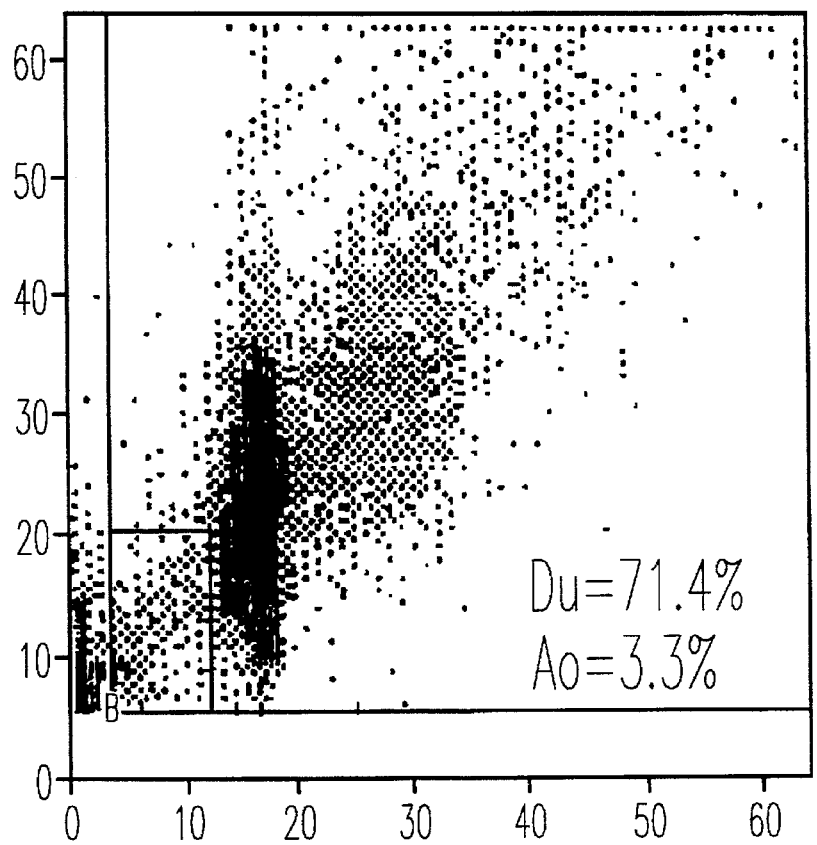
Figure 6:
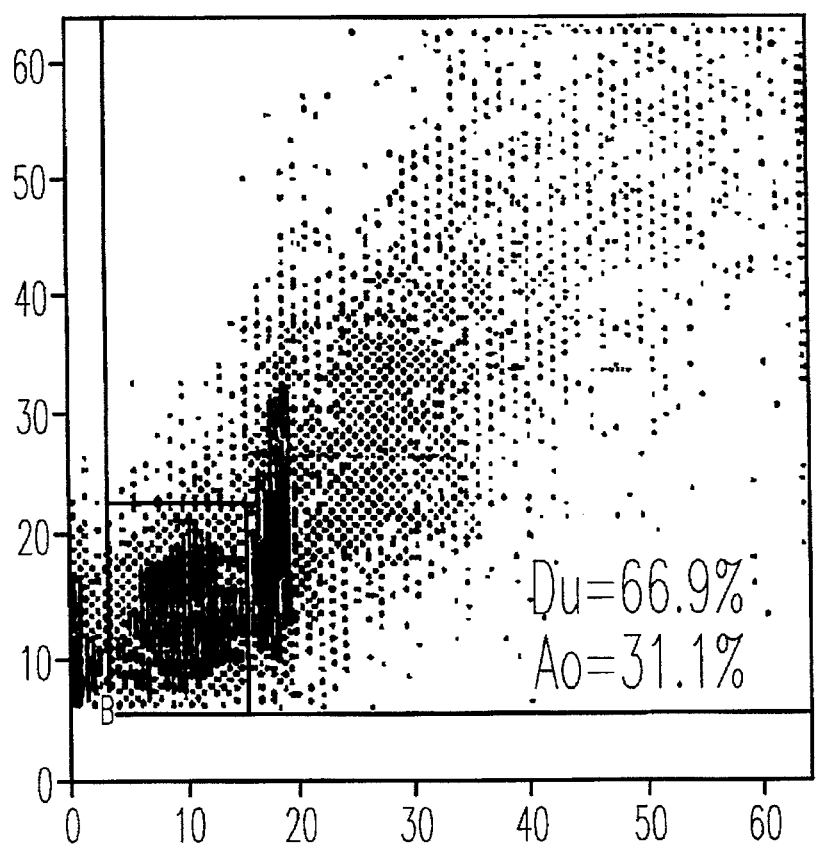

The present invention provides a method for selectively inducing apoptosis by enhancing the action of hydroxy radicals against the DNA of a particular type of target tissue compared to non-target tissue. The method comprises administering to a mammalian or human host a sensitizing agent and an oligonucleotide, either separately or concomitantly, wherein the compound is preferential for a certain target site in-vivo, such as a cancer cell.

Oligonucleotides complementary to and hybridizable with any portion of the MRNA transcript of p53, p21, CDC-2, CDK, or DNA polymerase β are, in principle, effective for inhibiting translation of the transcript, and capable of inducing the effects herein described. However, it is known that there are preferred sites to which the oligonucleotide is most preferably directed. For example, with respect to p53, translation is most effectively inhibited by blocking the mRNA at a site within a region defined by exon 10 or exon 11(i.e., the oligonucleotide is complementary to a portion of exon 10 or exon 11 of p53 mRNA).

Oligonucleotides hybridizable to the mRNA transcript finding utility according to the present invention include not only native polymers of the biologically significant nucleotides, but also oligonucleotide species which have been modified for improved stability and/or lipid solubility. For example it is known that enhanced lipid solubility and/or resistance to nuclease digestion results by substituting a methyl group or sulfur group in the internucleotide phosphodiester linkage. The phosphorothioates, in particular, are stable to nuclease cleavage and lipid-soluble. Consequently second and later generation molecular modifications of the native oligomer are included within the scope of this invention The sensitizing agent is an agent that increases the sensitivity of a cell to the effects of a cytotoxic, oxygen-generating agent. The oxygen-generating agent may be an oligonucleotide antisense to any of the mRNA of any of the oxygen radical scavenger proteins, a chemotherapeutic agent, or radiosensitizer, such as BSO, or any compound which will increase the amount of hydroxy radicals in the cell.

Usually such agents are not specific for a particular type of cell, which results in both normal and malignant cells becoming sensitized. Malignant cells, however, are already more susceptible to the effects of hydroxy radicals, resulting in a larger therapeutic index for the sensitizing agent.

In one embodiment of the invention, antisense oligonucleotides designed to the mRNA of the tumor suppressor gene p53 were shown in vitro to inhibit or kill tumor cell targets in a nucleic acid sequence specific manner.

The anti-p53 oligonucleotides can be synthesized and purified according to published methods for oligonucleotide synthesis. These methods are generally described, for example, in Stec and Zon, *J. Chromatogr* 326: 263, 1985; Iyer et al. (*Nucl. Acids Res.* 18: 2855, 1990; U.S. Pat. No. 5,264,423, European Patent Application EP 0 288 163 A2, or Winnacker, From *Genes to Clones: Introduction to Gene Technology*, VCH Verlagsgesellschaft mbH (H. Ibelgaufts trans. 1987).

While any of the known methods for oligonucleotide synthesis can be used to prepare the anti-p53 oligonuloetides, they are most conveniently prepared using any of the commercially available, automated nucleic acid synthesizers. The phosphorothioate antisense oligonucleotides of SEQUENCE ID NOS: 1–2 were prepared using an Applied Biosystems, Inc. DNA synthesizer (Model 380B) according to the manufacturer's protocols using phosphoramidite chemistry.

The following examples demonstrate that oligonucleotides directed to the p53 gene mechanically kill cells through apoptosis and that cell death is increased in the presence of oxygen radicals.

For examples 1–3, the phosphorothioate oligonucleotides used were from the group consisting of: OL(1)p53, (SEQ ID NO: 1) directed against a region in Exon 10 of p53; p53t, (SEQ ID NO:2) directed against a region in Exon 11 of p53; ISIS-1082 (5'-TCCTAGGTCC ATGTCGTACGC-3'; SEQ ID NO:3), a control sequence directed against a region in Herpes Virus; and FRED (5'-CCTCGGTCCC CCCTCGTCCC-3'; SEQ ID NO:4), a control sequence with the reverse orientation of SEQ ID NO:i (OL(1)p53). Oligonucleotides were synthesized on an Applied Biosystems (Foster City, Calif.) Model 380A DNA synthesizer. Phosphorothioate oligonucleotides were synthesized and purified according to the methods described in Stec and Zon, *J. Chromatog.*, 326: 263–280, and in *Applied Biosystems, DNA Synthesizer, User Bulletin*, Model 380A/380B/381A/391-EP, December 1989.

EXAMPLE 1

Oligonucleotide-Induced Lipid Peroxidation

Methods for Human Patients.

Three human patients with acute myelogenous leukemia or myelodisplastic syndrome were administered the oligonucleotide OL(1)p53 at a dose of 0.2 mg/kg/hr over a ten (10) day period. Urine samples were collected. 1 ml of 30 mM thiobarbituric acid (TBAR) and 500 µL of 1% trichloroacetic acid was added to 500 µL of urine. The samples were acidified to pH 1.5 with concentrated hydrochloric acid (HCl) and heated to 100° C. for 45 minutes and read at 532 nm using a spectrophotometer (Gilford) to determine the amount of TBAR products in the urine.

Results.

Human data indicates that the amount of TBAR in the urine increases with the level of OL(1)p53 in-vivo. (TABLE 1) In particular, a dramatic increase in TBAR can be seen after 7 days exposure to the oligonucleotide. Thiobarbituric acid reacts with a by-product of lipid peroxidation to provide colorometric detection. These data indicate that lipid peroxidation increase is dose dependent following seven days of exposure to oligonucleotide, which is not sequence dependent and can be observed in humans.

TABLE 1

| Thiobarbituric Acid Products Found in the Urine (Human) | | | | | | | |
|---|---|---|---|---|---|---|---|
|  | Day 0 | Day 2 | Day 4 | Day 5 | Day 6 | Day 7 | Day 8 |
| Pt. 12 | 1.0 .012* | 1.0 .012* | 1.3 .015* | a. | 1.1 .013* | a. | 1.8 .021* |
| Pt. 13 | 1.0 .094* | a. | a. | 0.8 .071* | a. | a. | a. |
| Pt. 14 | 1.0 .094* | a. | a. | a. | a. | 1.8 .168* | a. | a. No measurement was taken on this day.
*= actual absorbance value.

EXAMPLE 2

Effect of Oxidation State on Oligonucleotide Toxicity

Materials and methods.

Chang human liver cells were set up in a 96-well plate at 1500 cells/well. Oligonucleotides were added at a concentration of 3 µM ( (−) oligo, p53t, OL(1)p53, and ISIS1082).

Four wells for each oligonucleotide were set up under the conditions to be described. 1 µM of ascorbate (Sigma Chemical Co.) was added to one well of each oligo and the plates were incubated for 24 hours. 10 µM of hydrogen peroxide ($H_2O_2$) and 100 µM of zinc sulfate ($Zn\ SO_4$) each were added to separate wells of each oligo. The final well for each oligo was not altered. The plates were incubated for an additional 24 hours. An MTT (3-[4,5-dimethylthylthiazol-2-yl]-2,5-diphenyltetrazolium bromide) Assay was conducted on the 96-well plate to determine the amount of cell death which occurred in each well.

MTT Assay.

5 mg/ml of MTT was added to each of the wells on the 96-well plate. The plate was incubated for 2 hours. The MTT was removed from the plate and 100 µL of dimethylsulfoxide (DMSO) was added to each well. The optical density (OD) of each well was determined at 540 nm on a Molecular Devices Plate Reader.

Results.

OL(1)p53 alone resulted in a 17% increase in cell death over the control. Administration of p53t to the liver cell culture resulted in a 12% death of the cells. No cell killing was observed with the control oligonucleotide. When ascorbate was added to the media, the p53 induced cell death was eliminated for both the p53t and the OL(1)p53 oligonucleotides. In contrast, when hydrogen peroxide was added to the media, the amount of cell killing induced by p53 was 29% for OL(1)p53 and 19% for p53t. The addition of ZnSO4 resulted in 23% cell killing with OL(1)p53 and 19% with p53t (TABLE 2). These results show that the addition of an oxygen scavenger will decrease the rate of cell death and the addition of an oxygen generator will increase the rate of cell death when used in conjunction with an antisense oligonucleotide directed to the p53 mRNA. It appears that cell death induced by p53 antisense oligonucleotides is mediated through oxygen radicals. These results are p53 specific.

TABLE 2

Chang Cell Killing by Oligonucleotides
(% Increase in Cell Death vs. Control)

| CONDITION | p53t* | OL(1)p53* | ISIS 1082 |
| --- | --- | --- | --- |
| Oligo Only | 12% | 17% | 0% |
| Oligo + Ascorbate | 0% | 0% | 0% |
| Oligo + ZnSO$_4$ | 19% | 23% | 2% |
| Oligo + H$_2$O$_2$ | 18% | 29% | 0% |

The following example demonstrates the ability of antisense oligonucleotides, directed toward the p53 gene, to increase the rate of cell death through the mechanism of apoptosis.

EXAMPLE 3

Oligonucleotide-Induced Apoptosis

Cell cultures.

Blast cells from peripheral blood samples of two patients with acute myelogenous leukemia (AML) were used. Primary suspension cultures were performed according to the methods described by Bayever et. al. (Leukemia and Lymphoma). Leukemic blasts were isolated from heparinized peripheral blood by Ficoll-Hypaque (Pharmacia LKB Biotechnology, Piscataway, N.J.) separation and depleted of T-cells adhered to AET-treated sheep-erythrocyte (Sigma, St. Louis, Mo.). The cells were cultured at $5\times10^5$/ml in 24-well plates in Iscove's medium (Sigma), 12.5% FCS (Hyclone Laboratories, Logan, Utah), 12.5% horse serum (GIBCO, Grand Island, N.Y.), 1 µg/ml Gentamicin (Sigma) and 1% hydrocortisone (Abbott Laboratories, Chicago, Ill.) in humid air 5% $CO_2$ at 37° C and oligonucleotides (OL(1) p53, SEQ. ID. NO. 1; and FRED) were added 24 hours later at 1 µM. Viable cell counts were determined by Trypan blue exclusion from aliquots removed every 2 to 3 days. On day 10–12 of culture, cells were harvested and cultures continued in the absence of oligonucleotides.

Control apoptotic cells.

To provide control apoptotic cells, thymocytes were obtained from young (4–6 week old) BDF1 mice supplied by Jackson Laboratories, Bar Harbor, Me. The mice were humanely euthanized, and thymic tissue removed and minced. A cell suspension was prepared by repeated gently aspiration of the cells into a 1 ml syringe without a needle. The cells were washed 3 times and gently resuspended in RPMI 1640 with 20% fetal calf serum at $2\times10^6$ cells/mi. The thymocytes were then treated with dexamethasone (1 µM/4 hours) or hydrocortisone acetate at 10 µM (overnight). These cells were then employed as control apoptotic cells for flow cytometry.

Flow Cytometry.

Quantitation of viable cells, apoptotic cells and cell cycle fractions was carried out essentially according to the following procedure: $2\times10^5$ cells from each well were fixed in 1 ml cold 70% ethanol for 1 hour at 4° C. The cells were centrifuged and resuspended in 1 ml PBS containing 0.1% Triton X-100, 0.1 mM (ethylenediaminetetraacetic acid) EDTA, 50 µg/ml RNase (50 units/mg) and 50 µg/ml propidium iodide (Sigma, St. Louis, Mo.). The cells were incubated overnight at 4° C. and then allowed to warm to room temperature for 30 minutes in the dark prior to analyzing. Cells were then analyzed on an EPICS Elite flow cytometer using Coulter software. The percentage of apoptotic cells was calculated from the forward angle light scatter (FS) versus linear red fluorescence histogram by gating on the $A_o$ population. Apoptotic cell numbers were expressed as a percentage of total cells incorporating dye after exclusion of non-staining, non-viable cells and debris. For each sample $10^4$ cell events were recorded on the FS versus linear red fluorescence histogram.

Results.

Cell number and percent viability determinations were made using propidium iodide dye exclusion assayed by flow cytometry in selected suspension cultures of AML cells. The flow cytometry graphs indicate that the percentage of apoptotic cells increases with the addition of oligonucleotide. (FIG. 1) The percentage of intact, actively cycling cells is represented by $D_u$ and the percentage of apoptotic cells is represented by $A_o$. OL(1)p53 had a consistent inhibitory effect on the in vitro growth and viability of leukemia blast cells from the peripheral blood of patients with acute myelogenous leukemia (AML). The induction of enhanced apoptosis following cell exposure to the oligonucleotide is at least partially responsible for the cell death observed.

EXAMPLE 4

The following prophetic example demonstrates the invention's usefulness in the treatment of human B-cell lymphoma.

Drug Treatment Regimen: Starting on Day 0, patients receive SEQ ID NO:1 (OL(1)p53) at a dose of 0.2 mg/kg/hr as a 7 day continuous IV infusion through a venous access device. MINE chemotherapy is given beginning on Day 4, in accordance with the following schedule:

Mesna Injection (MESNEX, Bristol-Meyers Oncology): 500 mg/MIV 30 minutes prior to ifosfamide, 250 mg/M$^2$ IV four hours after ifosfamide, and 250 mg/M$^2$ orally eight hours after the ifosfamide on each of days 4 through 7.

Ifosfamide (IFEX, Bristol-Meyers Oncology): 1.33 g/M2 IV on each of days 4 through 7.

Mitoxantrone hydrochloride (NOVANTRONE, Lederle Laboratories) 10 mg/M$^2$ IV on day 4 only.

Etoposide (VEPESID, Bristol-meyers Oncology) 80 mg/M2 IV on each of days 4 through 7.

Patients are regularly evaluated for toxicity and response of their disease. Patients receive weekly CBC (complete blood count) and platelet counts. Cycles are repeated every 4 weeks for a maximum of 6 cycles. Patients are assessed with respect to response every cycle for disease measurable by physical examination. Patients are classified with respect to response (complete response, partial response, stable response, or progressive disease).

Patients are expected to show enhanced clinical response with this therapy as opposed to traditional MINE therapy, which does not include use of the antisense oligonucleotide SEQ ID NO:I (OL(1)p53). OL(1)p53 is expected to sensitize the cancer cells to the effects of MINE by inhibiting the cell cycle repair mechanism, thereby preferentially killing cancer cells via p53-independent apoptosis.

In accordance with the present invention, the oligonucleotide which acts as an oxidative repair path down-regulator is administered to a patient prior to, substantially concomitantly with, or simultaneously with administration of the agent capable of radical oxygen induced cytotoxicity. When administered simultaneously, the two active agents can be in conjugated or unconjugated form. The amount of each agent administered is such that the combination of the two types of agents is therapeutically effective. The dosages will vary in accordance with such factors as the condition of the patient, the type of cancer being treated, the type of agents being administered. In this regard, the cytotoxic reactive oxygen increasing agents generally preferred are those well known in the art. Recommended dosages and dosage forms for most of these agents have been established and can be obtained form conventional sources, such as the Physicians Desk Reference, published by Medical Economics Company, Inc., Oradell, N.J. 07649 or the Merck Index, published by Merck & Co., Inc., Whitehouse, N.J.

In one embodiment of the invention, a method for treating cancer characterized by p53 expression is provided. (Such cancers include those of the bladder, brain, breast, cervix, colon, esophagus, larynx, liver, lung, ovary, pancreas, prostate, skin, stomach and thyroid.) An oligonucleotide effective against the type of cancer with which a patient is afflicted is administered to the patient prior to or substantially concomitantly with administration of an agent capable of radical oxygen induced cytotoxicity (and which effectively increases the net reactive oxygen content of the cells upon exposure thereto). When the oligonucleotide and the reactive oxygen increasing cytotoxic agent are administered simultaneously, they can be given to the patient either separately or in conjugated form. It is preferred that each immunoconjugate comprises a cleavable linkage so that the oligonucleotide and the cytotoxic agent are released at the target site.

Those skilled in the medical oncology arts will readily appreciate that the doses and schedules of the free oligonucleotide, the free agent capable of radical oxygen induced cytotoxicity the conjugated oligonucleotide/agent will vary depending on the age, health, sex, size and weight of the patient, the route of administration, the toxicity of the drugs and the relative susceptibilities of the cancer to the oligonucleotide and cytotoxic agent. These parameters can be determined for each system by well-established procedures and analysis e.g., in phase I, II and III clinical trials.

For in vivo use, the preferred dosage of the oligonucleotides of the present invention is that which is necessary to attain a concentration in blood of from about 0.01 to about 1 micromoles/l. This concentration can be achieved in a variety of ways. Doses of between about 0.05 and about 0.2 mg/kg/hour by continuous IV infusion has been found to be acceptable. Greater or lesser amounts of oligonucleotide may be administered as required.

For such administration the antisense oligonucleotides, or conjugates thereof, can be combined with a pharmaceutically acceptable carrier, such as a suitable liquid vehicle or excipient and an optional auxiliary additive or additives. The liquid vehicles and excipients are conventional and commercially available. Illustrative thereof are distilled water, physiological saline, aqueous solutions of dextrose and the like. For in vivo antineoplastic use, the p53 mRNA antisense oligonucleotides are preferably administered intravenously.

In general, in addition to the active compounds, the pharmaceutical compositions of this invention may contain suitable excipients and auxiliaries which facilitate processing of the active compounds into preparations which can be used pharmaceutically. Oral dosage forms encompass tablets, dragees, and capsules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example, the pharmaceutical preparations may be made by means of conventional mixing, granulating, dragee-making, dissolving, or lyophilizing processes. The process to be used will depend ultimately on the physical properties of the active ingredient used.

Suitable excipients are, in particular, fillers such as sugars, for example, lactose or sucrose, mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethylstarch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate, and/or polyethylene glycol. Dragee cores may be provided with suitable coatings which, if desired, may be resistant to gastric juices.

For this purpose, concentrated sugar solutions may be used, which may optionally contain gum arabic, talc, polyvinylpyrrolidone, polyethylene glycol, and/or titanium dioxide, lacquer solutions, and suitable organic solvents or solvent mixtures. In order to produce coatings resistant to gastric juices, solutions of suitable cellulose preparations such as acetylcellulose phthalate or hydroxypropylmethylcellulose phthalate, are used. Dyestuffs and pigments may be added to the tablets of dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added. Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include, for example liquid triglycerides, polyethylene glycols, or paraffin hydrocarbons.

Suitable formulations for parenteral administration include aqueous solutions of the active compounds in water-soluble or water-dispersible form. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran, optionally, the suspension may also contain stabilizers.

In addition to administration with conventional carriers, the active ingredients may be administered by a variety of specialized delivery techniques. For example, the compounds of the present invention may also be administered encapsulated in liposomes, pharmaceutical compositions wherein the active ingredient is contained either dispersed or variously present in corpuscles consisting of aqueous concentric layers adherent to lipidic layers. The active ingredient, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, more or less ionic surfactants such as diacetylphosphate, stearylamine, or phosphatidic acid, and/or other materials of a hydrophobic nature. The diameters of the liposomes generally range from about 15 nm to about 5 microns.

What is claimed is:

1. A method for killing cancer cell comprising:
   a) exposing the cancer cells to an effective amount of an antisense oligonucleotide, and
   b) exposing the cancer cells to an effective amount of free hydroxy radicals.

2. The method claim 1 wherein said antisense oligonucleotide has a sequence selected from the group consisting of:

5'-CCCCTGCTCCC CCCTGGCTCC-3'
SEQUENCE ID NO: 1

5'-AGCAGGGCTC ACTCCAGC-3'
SEQUENCE ID NO: 2.

3. The method of claim 1 wherein a radiosensitizer is employed to increase the amount of free hydroxy radicals.

4. The method of claim 3 wherein aid radiosensitizer is selected from the group consisting of zinc sulfate, hydrogen peroxide, buthionine sulfoximine, and sulfoxamide dismutase.

5. The method of claim 1 wherein the free radicals are produced by an effective amount of a radiosensitizing agent.

6. The method of claim 1 wherein the free radicals are produced in an oxygen-rich atmosphere.

7. The method of claim 1 wherein the free radicals are produced by ionizing radiation.

8. The method of claim 5 wherein said radiosensitizing agent is an oxygen generator.

9. A pharmaceutical composition comprising a pharmaceutical carrier, an agent capable of generating free oxygen radicals, and an antisense oligonucleotide.

10. The method of any one of claims 1 wherein said antisense oligonucleotide comprises an alternating sequence of nucleoside moieties and linkage moieties such that the linkage moieties are selected from the group consisting of phosphorothioate, methylphosphonate, phosphorotriester, and phosphodiester.

11. The pharmaceutical composition of claim 9, wherein said antisense oligonucleotide comprises an alternating sequence of nucleoside moieties and linkage moieties such that the linkage moieties are selected from the group consisting of phosphorothioate, methylphosphonate, phosphorotriester, and phosphodiester.

\* \* \* \* \*

UNITED STATES PATENT AND TRADEMARK OFFICE
CERTIFICATE OF CORRECTION

PATENT NO. : 5,641,754 Page 1 of 1
APPLICATION NO. : 08/179655
DATED : June 24, 1997
INVENTOR(S) : Patrick L. Iversen It is certified that error appears in the above-identified patent and that said Letters Patent is hereby corrected as shown below:

Column 5, line 6: should read --5'-GCTGGAGTGAGCCCTGCT-3'--
Column 13, line 67: should read --GCTGGAGTGAGCCCTGCT--
Column 15, line 46: should read --5'-GCTGGAGTGAGCCCTGCT-3'--

Signed and Sealed this

Tenth Day of July, 2007

JON W. DUDAS
*Director of the United States Patent and Trademark Office*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:1:

CCCTGCTCCC CCCTGGCTCC        20

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:2:

AGCAGGGCTC ACTCCAGC        18

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:3:

TCCTAGGTCC ATGTCGTACG C      21

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CCTCGGTCCC CCCTCGTCCC      20